US012723013B2

(12) United States Patent
Zhou et al.

(10) Patent No.: US 12,723,013 B2
(45) Date of Patent: Sep. 1, 2026

(54) METHOD FOR PREPARING BIO-BASED 1,4-BUTANEDIOL

(71) Applicant: ZHEJIANG BOJU NEW MATERIALS CO., LTD., Zhejiang (CN)

(72) Inventors: Minghe Zhou, Zhejiang (CN); Jun Zhou, Zhejiang (CN); Bihong Xu, Zhejiang (CN)

(73) Assignee: Zhejiang Boju New Materials Co., Ltd., Zhejiang (CN)

( * ) Notice: Subject to any disclaimer, the term of this patent is extended or adjusted under 35 U.S.C. 154(b) by 0 days.

(21) Appl. No.: 18/797,010

(22) Filed: Aug. 7, 2024

(65) Prior Publication Data

US 2025/0051252 A1 Feb. 13, 2025

(30) Foreign Application Priority Data

Aug. 7, 2023 (CN) ........................ 202310983414.X

(51) Int. Cl.

| | |
|---|---|
| ***C07C 29/147*** | (2006.01) |
| ***B01J 23/72*** | (2006.01) |
| ***B01J 37/04*** | (2006.01) |
| ***C07C 29/74*** | (2006.01) |

(52) U.S. Cl.

CPC ............. *C07C 29/147* (2013.01); *B01J 23/72* (2013.01); *B01J 37/04* (2013.01); *C07C 29/74* (2013.01)

(58) Field of Classification Search

CPC ........ C07C 29/147; C07C 29/74; B01J 23/72; B01J 37/04

See application file for complete search history.

(56) References Cited

U.S. PATENT DOCUMENTS 6,107,446 A * 8/2000 Loza et al. ............. C08G 63/02 528/272

FOREIGN PATENT DOCUMENTS

| | | | |
|---|---|---|---|
| CN | 101244984 | A | 8/2008 |
| CN | 102408307 | A | 4/2012 |
| CN | 106083523 | A | 11/2016 |
| CN | 107915579 | A | 4/2018 |
| CN | 108017509 | A | 5/2018 |
| CN | 109651110 | A | 4/2019 |
| CN | 110563553 | A | 12/2019 |
| CN | 111801312 | A | 10/2020 |
| CN | 113683483 | A | 11/2021 |

(Continued)

OTHER PUBLICATIONS

Catal. Sci. Technol. 2011, 1, 111-122 (Zhou et al.) (Year: 2011).*

(Continued)

*Primary Examiner* — Amy C Bonaparte
*Assistant Examiner* — Derek Rhoades
(74) *Attorney, Agent, or Firm* — Bryan D. Zerhusen, Esq.; Nicholas R. Herrel, Esq.; CANTOR COLBURN LLP

(57) ABSTRACT

A method for preparing bio-based 1,4-butanediol (BDO) is provided, including: mixing succinic acid from a bio-based source and an alcohol compound to obtain a mixture, and subjecting the mixture to esterification to obtain an oligomer polyester; subjecting the oligomer polyester to hydrogenation reduction in the presence of a catalyst to obtain a 1,4-BDO crude product; and purifying the 1,4-BDO crude product to obtain the bio-based 1,4-BDO.

7 Claims, 1 Drawing Sheet

(56) References Cited

FOREIGN PATENT DOCUMENTS

| | | | | |
|---|---|---|---|---|
| CN | 114524707 A | * | 5/2022 | ........... C07C 29/149 |
| CN | 117003614 B2 | | 11/2023 | |

OTHER PUBLICATIONS

CN 114524707 A; (Zhou et al.; English language machine translation) (Year: 2022).*
Practical Process & Research Development, 2000, pp. 169-170 (Anderson) (Year: 2000).*
Notification of Grant Patent Right for Invention for CN202310983414.X Dated Apr. 30, 2025.
Office Action Issued Feb. 13, 2025, for CN202310983414.X.
Zhang, J., et al, Rapic synthesis of 2-aminomethylbenzimidazole by microwave radiation, vol. 25, Speciality Petrochemicals, pp. 19-21, Jan. 18, 2008.
Zheng Ya-qing, et al., Synthesis of Propiconazole Intermediate 1,2-Pentanediol, Agrochemicals, vol. 53, No. 2, Feb. 2014, pp. 96-98 (abstract in English).

* cited by examiner

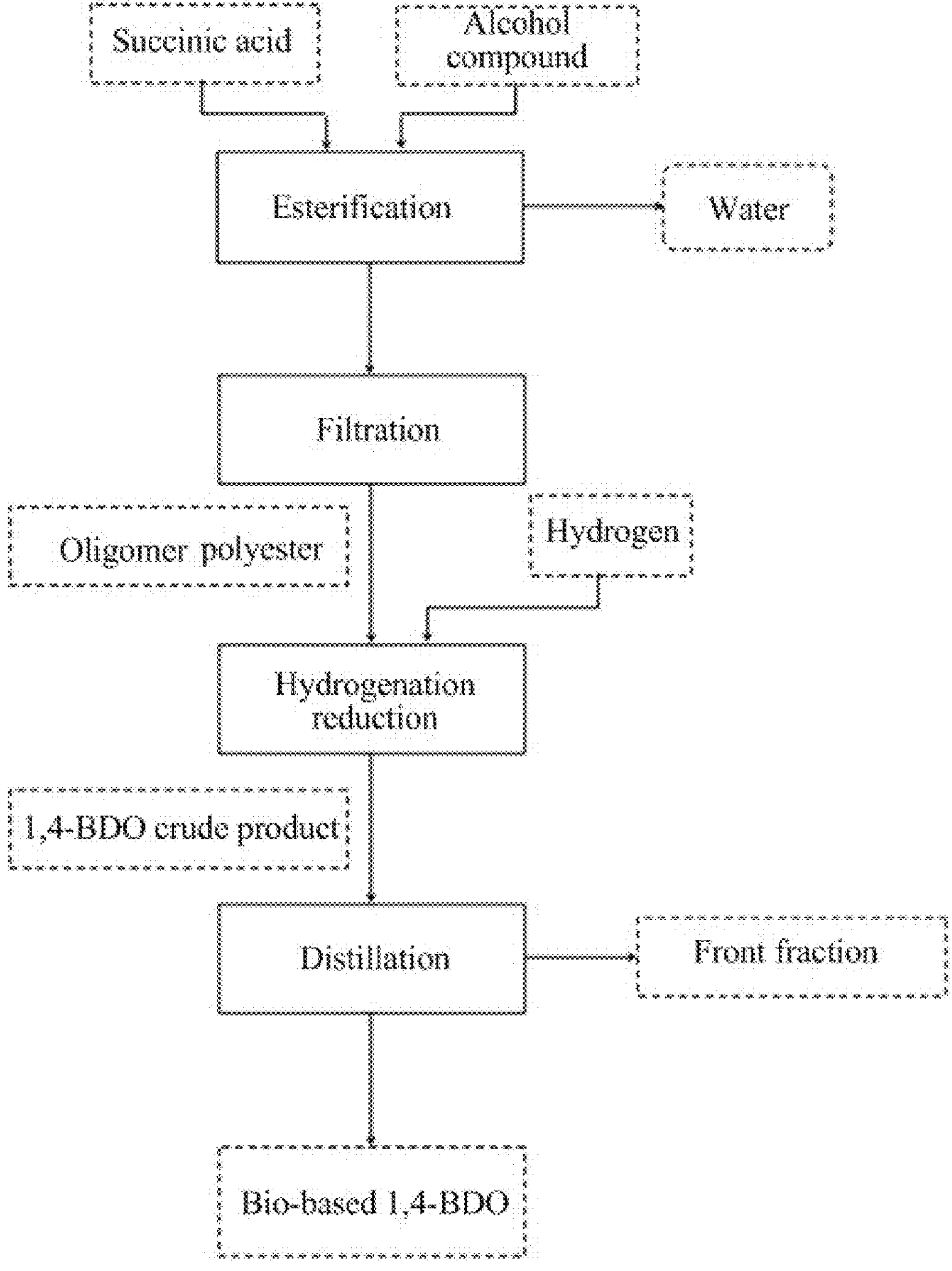
Succinic acid
Alcohol compound
Esterification
Water
Filtration
Oligomer polyester
Hydrogen
Hydrogenation reduction
1,4-BDO crude product
Distillation
Front fraction
Bio-based 1,4-BDO

METHOD FOR PREPARING BIO-BASED 1,4-BUTANEDIOL

CROSS REFERENCE TO RELATED APPLICATION

This patent application claims the benefit and priority of Chinese Patent Application No. 202310983414.X filed with the China National Intellectual Property Administration on Aug. 7, 2023, and entitled with "METHOD FOR PREPARING BIO-BASED 1,4-BUTANEDIOL", the disclosure of which is incorporated by reference herein in its entirety as part of the present application.

TECHNICAL FIELD

The present disclosure relates to the technical field of organic synthesis, and in particular to a method for preparing bio-based 1,4-butanediol (BDO).

BACKGROUND 1,4-Butanediol (BDO) is a transparent liquid at room temperature, has desirable chemical stability, and serves as an important chemical raw material that can be used in pharmaceutical synthesis as well as the preparation of advanced coatings, advanced inks, advanced resins, synthetic fiber rubber, and surfactants.

At present, the main production processes for 1,4-BDO include the Reppe method, the maleic anhydride method, the allyl alcohol method, and the butadiene method. In these traditional methods a petrochemical-based compound is used as a raw material source. In the Reppe method, acetylene and formaldehyde are used as raw materials. 1,4-Butynediol is synthesized from the acetylene and formaldehyde under the action of a copper catalyst and then is hydrogenated to produce 1,4-BDO. The Reppe method has advantages, such as low operating costs, but there is a relatively high acetylene partial pressure in the acetylation process, resulting in the process requiring a reactor design safety factor of up to 12 to 20, which greatly increases the initial equipment investment cost. Further, the high acetylene partial pressure is also prone to produce polyacetylene, which leads to pipeline blockage, reduces production efficiency, and easily causes catalyst deactivation. In view of the shortcomings of the traditional Reppe method, an improved Reppe method is safer, requires less equipment investment, and has a longer production cycle. The improved Reppe method is mainly divided into four processes: BASF, Dupont, IS, and Linde & SK. For example, Chinese patent CN101244984A discloses a comprehensive method for continuously preparing 1,4-BDO, including the following stages: (I) subjecting formaldehyde and acetylene to a reaction in the presence of a copper catalyst at a pH value of 5 to 8, wherein a molar ratio of the formaldehyde to the acetylene is most 2:1; (II) subjecting a resulting aqueous mixture containing butynediol to intermediate buffering for 0.1 h to 100 h; (III) subjecting a mixture obtained after the intermediate buffering to hydrogenation; and (IV) distilling a hydrogenated product obtained in stage III to obtain the 1,4-BDO. Chinese patent CN102408307A discloses a method for preparing BDO by hydrogenation of butynediol in a two-stage bed. Aiming at the adaptability to the reaction system containing water or the fluctuation of water content in the reaction system in the current two-step hydrogenation of butynediol to prepare BDO and the requirement for inhibiting the formation of carbon deposits, the method proposes that the catalysts A and B for the hydrogenation in the two-stage bed contain carriers, metal active components, and silane groups, and the silane groups are grafted by silylation, wherein the silane groups account for 0.1 wt % to 12 wt % of a total weight of the catalysts for the hydrogenation. Compared with the prior art, on the premise of ensuring that the catalysts for the hydrogenation have desirable activity and selectivity, there is obvious raw material applicability, and the presence of water has almost no effect on the catalytic performance of the catalysts for the hydrogenation. Meanwhile, the method can significantly inhibit the formation of carbon deposits on the catalyst surface and prolong the service life of the catalyst, making the hydrogenation system have a longer stable operation cycle. Chinese patent CN109651110A discloses a production process, mainly including: a formaldehyde section, an ethynylation section, a hydrogenation section, and a product rectification section. The formaldehyde section mainly generates formaldehyde from a raw material methanol and air under the action of a catalyst; the rectification section mainly generates refined 1,4-butynediol by acetylene and the formaldehyde under the action of a catalyst; the hydrogenation section mainly generates crude 1,4-BDO by reacting the 1,4-butynediol and hydrogen from an upstream furnace gas purification section at a certain pressure under the action of a catalyst; and the product rectification section mainly conducts rectification on the crude 1,4-BDO to obtain high-purity 1,4-BDO.

In the butadiene method, butadiene is converted into 1,4-diacetoxy-2-butene by acetyl oxidation, and then the 1,4-diacetoxy-2-butene is further subjected to hydrogenation to obtain 1,4-diacetoxybutane, and finally, the 1,4-diacetoxybutane is hydrolyzed to obtain the target product 1,4-BDO. This method not only has the advantages of high selectivity for the target product and flexible control of the ratio of tetrahydrofuran (THF) to 1,4-BDO, but also has disadvantages such as high steam consumption and complex equipment. For example, Chinese patent CN108017509A discloses a method for producing 1,4-BDO from butadiene, including the following steps: subjecting butadiene, acetic acid, and oxygen as raw materials to oxyacetylation in the presence of an oxyacetylation catalyst to obtain 1,4-diacetoxybutene; in the presence of a hydrogenation catalyst, subjecting hydrogen to a reaction with the 1,4-diacetoxybutene to obtain 1,4-diacetoxybutane, and then subjecting the 1,4-diacetoxybutane to hydrolysis to obtain the 1,4-BDO. The catalyst for the hydrogenation uses activated carbon as a carrier, and the active component includes a Pt element and a cocatalyst element, and the cocatalyst element includes at least one metal element selected from the group consisting of the iron-based metals and VA group metals. Chinese patent CN107915579A discloses that butadiene, acetic acid, and oxygen are used as raw materials, and the raw materials are subjected to oxyacetylation in the presence of an oxyacetylation catalyst to obtain 1,4-diacetoxybutene; in the presence of a hydrogenation catalyst, hydrogen reacts with the 1,4-diacetoxybutene to obtain 1,4-diacetoxybutane, and then the 1,4-diacetoxybutane is hydrolyzed to obtain 1,4-BDO. The catalyst for the hydrogenation uses activated carbon as a carrier, and the active component includes a Pt element and a cocatalyst element, and the cocatalyst element includes at least one metal element selected from the group consisting of the metalloid group metal and the VIIB group metal.

In the allyl alcohol method, propylene oxide is isomerized into allyl alcohol. The allyl alcohol is subjected to liquid phase hydrocarbonylation in the aromatic hydrocarbon as a solvent under the action of a rhodium-based catalyst and triphenylphosphine solution as a catalyst to generate a 4-hydroxybutyraldehyde solution, which is then subjected to hydrogenation under the action of a Raney nickel catalyst to generate 1,4-BDO. This method uses rare precious metals that are expensive and not environmental-friendly, and has the disadvantages of low product selectivity and high content of by-products. For example, Chinese patent CN111801312A discloses that allyl alcohol in an allyl alcohol feed is subjected to hydrocarbonylation with a synthesis gas to produce a hydroformylation product including 4-hydroxybutyraldehyde and 3-hydroxy-2-methylpropanal, and a 1,4-BDO product including BDO and 1,3-methylpropanediol is produced by hydrogenating at least a portion of the hydroformylation product.

The maleic anhydride method uses maleic anhydride as a raw material to react with methanol to produce maleic dimethyl ester, and then the maleic dimethyl ester is subjected to hydrogenation to obtain 1,4-BDO and co-produce THF. This method has disadvantages, such as high raw material costs and large equipment investment. For example, Chinese patent CN106083523A discloses that a maleic anhydride production process is combined with a BDO production process, thus omitting equipment and energy consumption of the original oil-rich analysis and solvent treatment in the n-butane method maleic anhydride unit. Impurities produced by the maleic anhydride unit are removed together with those of the BDO unit, thereby saving the cost of the unit. Butanol is used as a raw material for maleic anhydride esterification to produce dibutyl maleate (DBM), such that the butanol as a by-product produced in the hydrogenation stage can be recycled.

In the above traditional methods, petrochemical-based compounds are used as a raw material source, but petrochemical-based raw materials are becoming increasingly scarce and non-renewable.

SUMMARY

In view of this, an object of the present disclosure is to provide bio-based 1,4-BDO, and a preparation method and use thereof. In the present disclosure, succinic acid from a bio-based source is used as the raw material to prepare the bio-based 1,4-BDO as the target product through esterification and hydrogenation reduction. The raw material has an extensive source and is renewable.

To achieve the above object, the present disclosure provides the following technical solutions:

The present disclosure provides a method for preparing bio-based 1,4-BDO, including:

- mixing succinic acid from a bio-based source and an alcohol compound to obtain a mixture, and subjecting the mixture to esterification to obtain an oligomer polyester;
- subjecting the oligomer polyester to hydrogenation reduction in the presence of a catalyst to obtain a 1,4-BDO crude product; and
- purifying the 1,4-BDO crude product to obtain the bio-based 1,4-BDO.

In some embodiments, the alcohol compound includes one or more selected from the group consisting of butanol, pentanol, hexanol, ethylene glycol, and 1,4-BDO.

In some embodiments, a molar ratio of the succinic acid from the bio-based source to the alcohol compound is in a range of 1:(1.2-2.4).

In some embodiments, the esterification is conducted at a temperature of 160° C. to 210° C. for 4 h to 8 h.

In some embodiments, a hydrogen-to-ester ratio of hydrogen used in the hydrogenation reduction to the oligomer polyester is in a range of (80-200):1.

In some embodiments, the hydrogenation reduction is conducted at a pressure of 1 MPa to 20 MPa and a temperature of 100° C. to 220° C. for 2 h to 6 h.

In some embodiments, the catalyst is a supported copper-based catalyst.

In some embodiments, the supported copper-based catalyst is prepared by a process including the following steps:

(1) mixing copper nitrate hexahydrate, aluminum nitrate nonahydrate, an active metal salt, and water to obtain a metal ion salt solution, wherein a metal in the active metal salt includes one selected from the group consisting of magnesium, manganese, nickel, cobalt, zinc, cerium, and zirconium;

(2) mixing sodium hydroxide, sodium carbonate, and water to obtain an alkaline solution precipitant, wherein molar weight (m) of hydroxy radical is calculated as follows: $m[OH^-]=2m([M^{2+}]+[M^{3+}])$, and molar weight (m) of carbonate radical is calculated as follows: $m[CO^{3-}]=0.5m[M^{3+}]$, with M referring to metal elements mentioned in step (1), i.e., copper, aluminum, and the metal in the active metal salt;

(3) adding the metal ion salt solution and the alkaline solution precipitant to a reactor at 60° C. to form a reaction system, and subjecting the reaction system to precipitation to obtain a precipitated product, wherein a pH value of the reaction system is maintained at a range of 8 to 10;

(4) aging the precipitated product at 70° C. for 24 h to obtain a ternary hydrotalcite-like compound; and (5) subjecting the ternary hydrotalcite-like compound to calcination and activation in sequence to obtain the supported copper-based catalyst.

In some embodiments, a molar ratio of the copper nitrate hexahydrate, the metal in the active metal salt, and the aluminum nitrate nonahydrate is in a range of (1-5):1:(0.25-2).

In some embodiments, the calcination is conducted at a temperature of 400° C. to 800° C. for 0.5 h to 8 h.

The present disclosure provides a method for preparing bio-based 1,4-BDO, including: mixing succinic acid from a bio-based source and an alcohol compound to obtain a mixture, and subjecting the mixture to esterification to obtain an oligomer polyester; subjecting the oligomer polyester to hydrogenation reduction in the presence of a catalyst to obtain a 1,4-BDO crude product; and purifying the 1,4-BDO crude product to obtain the bio-based 1,4-BDO.

Compared with the prior art, the present disclosure has the following beneficial effects:

In the present disclosure, the bio-based 1,4-BDO as the target product is prepared by the esterification and hydrogenation reduction using the succinic acid from a bio-based source and the alcohol compound as raw materials. The succinic acid is derived from biological fermentation, The raw materials have an extensive source and are renewable, thus reducing carbon emissions and realizing the recyclable utilization of biomass energy. The method can not only increase the added value of the product, but also reduce environmental pollution, as well as bring considerable economic benefits.

Furthermore, in the present disclosure, the alcohol compound includes one or more selected from the group consisting of butanol, pentanol, hexanol, ethylene glycol, and 1,4-BDO. The succinic acid and the alcohol compound can be subjected to esterification without a catalyst, no post-treatment is required after the esterification is completed, no catalyst needs to be separated, and no cumbersome post-treatment is required. In addition, the 1,4-BDO has a relatively high boiling point, which is greatly different from that of water, and can be separated from the water distillation fraction. The water produced by the esterification can be separated from the reaction system, allowing the esterification to proceed smoothly. At the same time, no other types of alcohol are introduced into the esterification, and an intermediate product does not need to be distilled and purified, and can be used in the next process.

Furthermore, in the present disclosure, the supported copper-based catalyst is used in the hydrogenation reduction. A hydrotalcite-like precursor is prepared by the constant pH coprecipitation method, and then an active Cu-based catalyst is finally prepared by calcination and decomposition. The coprecipitation method is used to significantly increase the metal loading capacity compared with that of the traditional impregnation method. At the same time, the surface morphology and the physicochemical properties of the supported copper-based catalyst can be modified by regulating the active metal ratio and the calcination temperature, so that the catalyst has a higher specific surface area, greater metal dispersion, suitable surface acidity and alkalinity, and desirable $Cu^+/Cu^0$ ratio. Therefore, the catalytic hydrogenation of the catalyst to the oligomer polyester can achieve a lower hydrogenation pressure (1 MPa to 20 MPa), a lower hydrogenation temperature (100° C. to 220° C.), and a lower hydrogen-to-ester ratio (at (80-200):1). Moreover, the oligomer polyester has a conversion rate of greater than or equal to 99.5%, while the 1,4-BDO has a selectivity of greater than or equal to 98.0%.

The data of examples show that the bio-based 1,4-BDO has a purity of greater than or equal to 99.5%, a raw material conversion rate of greater than or equal to 99.5%, and a 1,4-BDO selectivity of greater than or equal to 98.0%.

BRIEF DESCRIPTION OF THE DRAWING

FIGURE shows a flow chart of the method for preparing the bio-based 1,4-BDO according to an embodiment of the present disclosure.

DETAILED DESCRIPTION OF THE EMBODIMENTS

The present disclosure provides a method for preparing bio-based 1,4-BDO, including the following steps:

- mixing succinic acid from a bio-based source and an alcohol compound to obtain a mixture, and subjecting the mixture to esterification to obtain an oligomer polyester;
- subjecting the oligomer polyester to hydrogenation reduction in the presence of a catalyst to obtain a 1,4-BDO crude product; and
- purifying the 1,4-BDO crude product to obtain the bio-based 1,4-BDO.

In the present disclosure, unless otherwise specified, all raw materials used are commercially available products conventional in the art.

In the present disclosure, succinic acid from a bio-based source and an alcohol compound are mixed to obtain a mixture, and the mixture is subjected to esterification to obtain an oligomer polyester.

In the present disclosure, taking 1,4-BDO as an example, a principle of esterification is shown in the following formula:

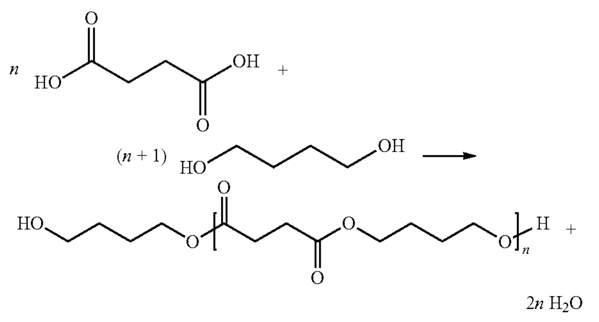

wherein, n is 1, 2, 3, 4, or 5.

In some embodiments of the present disclosure, the succinic acid from the bio-based source is derived from biological fermentation, and preferably starch fermentation or lignocellulose fermentation. In some embodiments of the present disclosure, a fermentation product is refined and purified to obtain the succinic acid, and a method familiar to those skilled in the art could be used. The succinic acid from a bio-based source has an extensive source and is renewable, thus reducing carbon emissions and realizing the recycling utilization of biomass energy. The method can not only increase an added value of the product, but also reduce environmental pollution, as well as bring considerable economic benefits.

In some embodiments of the present disclosure, the alcohol compound includes one or more selected from the group consisting of butanol, pentanol, hexanol, ethylene glycol, and 1,4-BDO, and preferably 1,4-BDO. The succinic acid and the alcohol compound can be subjected to esterification without a catalyst, no post-treatment is required after the esterification is completed, no catalyst needs to be separated, and no cumbersome post-treatment is required. In addition, the 1,4-BDO has a relatively high boiling point, which is greatly different from that of water, and can be separated from the water distillation fraction. The water produced by the esterification can be separated from the reaction system, allowing the esterification to proceed smoothly. At the same time, no other types of alcohol are introduced into the esterification, and an intermediate product does not need to be distilled and purified, and can be used in the next process.

In some embodiments of the present disclosure, a mass ratio of the succinic acid from the bio-based source to the alcohol compound is in a range of 10:(11-16).

In some embodiments of the present disclosure, the esterification is conducted at a temperature of 160° C. to 210° C., preferably 168° C. to 197° C., more preferably 175° C. to 190° C., and most preferably 182° C., and the esterification is conducted for 5 h to 7 h.

In some embodiments of the present disclosure, during the esterification, an acid value is controlled to be less than 10 mg KOH/g.

In some embodiments of the present disclosure, during the esterification, a sample is taken to detect and analyze an acid value and to detect a content of carboxylic acid therein; when the acid value is less than 10 mg KOH/g and reaches an esterification requirement, it is determined that the esterification is basically completed.

In some embodiments of the present disclosure, the acid value is analyzed by a process including the following procedures:

1. Regents and Test Solutions
   1.1 Anhydrous ethanol;
   1.2 Potassium hydroxide ethanol standard solution [C(KOH)=0.1 mol/L];
   1.3 Phenolphthalein indicator solution: 1 g/L ethanol solution; and
   1.4 Neutral ethanol: using phenolphthalein as an indicator, and adding dropwise the potassium hydroxide ethanol standard solution to the anhydrous ethanol until it turns slightly red.
2. Steps:

20 g of sample (accurate to 0.0001 g) is weighted and added to a conical flask, 50 mL of neutral ethanol, and 2 to 3 drops of phenolphthalein indicator are added thereto, and the potassium hydroxide standard solution is added dropwise thereto until it turns slightly red. If the solution does not fade within 10 s, the process is considered as an end point.

BE01 acid value $X_1$ (mg KOH/g) is calculated according to formula (1):

$$X_1 = \frac{C \cdot V \times 56.1}{m} \qquad \text{formula (1)}$$

in the formula: C represents a concentration of the potassium hydroxide ethanol standard titration solution, in mol/L;

V represents a volume of the potassium hydroxide ethanol standard titration solution consumed in titrating the sample, in mL;

56.1 represents a constant; and m represents a mass of the sample, in g.

In some embodiments of the present disclosure, an arithmetic mean of the parallel determination results is taken as an analysis result.

In some embodiments of the present disclosure, after the esterification is completed, a resulting oligomer polyester is directly subjected to hydrogenation reduction without post-treatment.

In the present disclosure, the oligomer polyester is subjected to hydrogenation reduction in the presence of a catalyst to obtain a 1,4-BDO crude product.

In the present disclosure, taking 1,4-BDO as an example, for the hydrogenation reduction, a main reaction is shown as follows:

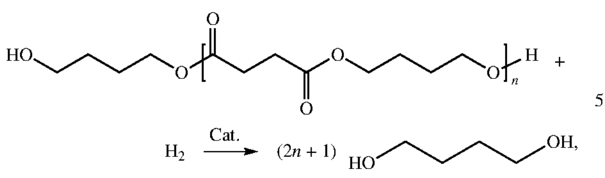

and a side reaction is shown as follows:

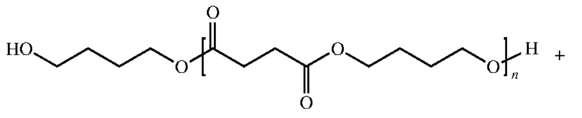

-continued

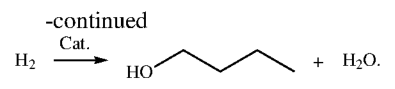

In some embodiments of the present disclosure, a hydrogen-to-ester ratio of hydrogen used in the hydrogenation reduction to the oligomer polyester is in a range of (80-200):1, wherein the hydrogen-to-ester ratio refers to a molar ratio of the hydrogen to the oligomer polyester.

In the present disclosure, the hydrogenation reduction is conducted at a pressure of 1 MPa to 20 MPa, preferably 8 MPa to 18 MPa, more preferably 10 MPa to 16 MPa, and most preferably 12 MPa to 14 MPa; the hydrogenation reduction is conducted at a temperature of 100° C. to 220° C., preferably 160° C. to 210° C., more preferably 170° C. to 200° C., and most preferably 180° C. to 190° C.; and the hydrogenation reduction is conducted for 2 h to 6 h, and preferably 3 h to 5 h.

In some embodiments of the present invention, a mass ratio of the catalyst to the oligomer polyester is in a range of 1:(500-1000).

In some embodiments of the present disclosure, the catalyst is a supported copper-based catalyst.

In some embodiments of the present disclosure, the supported copper-based catalyst is prepared by a process including the following steps:

(1) mixing copper nitrate hexahydrate, aluminum nitrate nonahydrate, an active metal salt, and water to obtain a metal ion salt solution, wherein a metal in the active metal salt includes one selected from the group consisting of magnesium, manganese, nickel, cobalt, zinc, cerium, and zirconium;

(2) mixing sodium hydroxide, sodium carbonate, and water to obtain an alkaline solution precipitant, wherein molar weight (m) of hydroxy radical is calculated as follows: $m[OH^-]=2m([M^{2+}]+[M^{3+}])$, and molar weight (m) of carbonate radical is calculated as follows: $m[CO^{3-}]=0.5m[M^{3+}]$, with M referring to metal elements mentioned in step (1), i.e., copper, aluminum, and the metal in the active metal salt;

(3) adding the metal ion salt solution and the alkaline solution precipitant to a reactor at 60° C. to form a reaction system, and subjecting the reaction system to precipitation to obtain a precipitated product, wherein a pH value of the reaction system is maintained at a range of 8 to 10;

(4) aging the precipitated product at 70° C. for 24 h to obtain a ternary hydrotalcite-like compound; and (5) subjecting the ternary hydrotalcite-like compound to calcination and activation in sequence to obtain the supported copper-based catalyst.

In some embodiments of the present disclosure, a molar ratio of the copper nitrate hexahydrate, the metal in the active metal salt, and the aluminum nitrate nonahydrate is in a range of (1-5):1:(0.25-2), and preferably (2-5):1:(0.3-0.7).

In some embodiments of the present disclosure, the calcination is conducted at a temperature of 400° C. to 800° C., and preferably 500° C. to 600° C., and the calcination is conducted for 0.5 h to 8 h, and preferably 2 h to 4 h.

In some embodiments of the present disclosure, the activation is conducted in 5 vol % $H_2$/Ar.

In some embodiments of the present disclosure, the hydrogenation reduction is conducted in a hydrogenation tower, and the catalyst is loaded in a continuous reactor.

In some embodiments of the present disclosure, a hydrotalcite-like precursor is prepared by the constant pH coprecipitation method, and then an active Cu catalyst-based is finally prepared by calcination and decomposition. The coprecipitation method is used to significantly increase the metal loading capacity compared with that of the traditional impregnation method. At the same time, the surface morphology and the physicochemical properties of the supported copper-based catalyst can be modified by regulating the active metal ratio and the calcination temperature, so that the catalyst has a higher specific surface area, greater metal dispersion, suitable surface acidity and alkalinity, and desirable $Cu^{+}/Cu^{0}$ ratio. Therefore, the catalytic hydrogenation of the catalyst to the oligomer polyester can achieve a lower hydrogenation pressure, a lower hydrogenation temperature, and a lower hydrogen-to-ester ratio, while increasing the conversion rate of the oligomer polyester and the selectivity of the 1,4-BDO.

In the present disclosure, the 1,4-BDO crude product is purified to obtain the bio-based 1,4-BDO.

In some embodiments of the present disclosure, the purifying is conducted by rectifying and purifying, and the rectifying and purifying is conducted at a pressure of 8 mmHg to 25 mmHg, and the rectifying and purifying is conducted at a temperature of 140° C. to 190° C.

In some embodiments of the present disclosure, a front fraction is obtained from the rectifying and purifying, and the front fraction includes n-butanol, water, and THE, and the front fraction is used as a by-product solvent.

In some embodiments of the present disclosure, a high-boiling component is obtained as a by-product from the rectifying and purifying.

To further describe the present disclosure, the method for preparing bio-based 1,4-BDO provided by the present disclosure will be described in detail below with reference to examples. However, these examples should not be construed as limitations to the scope of the present disclosure.

FIGURE shows a flow chart of the method for preparing bio-based 1,4-BDO according to an embodiment of the present disclosure.

A supported copper-based catalyst used in Examples 1 to 7 of the present disclosure was prepared by a process consisting of the following steps:

(1) 2.4 mol of aluminum nitrate nonahydrate, 1 mol of zinc nitrate hexahydrate, and 0.6 mol of water were mixed to obtain a metal ion salt solution.

(2) Sodium hydroxide, sodium carbonate, and water were mixed to obtain an alkaline solution precipitant, wherein a molar ratio includes $[OH^{-}]=2([M^{2+}]+[M^{3+}])$ and $[CO^{3-}]=0.5[M^{3+}]$, and M referes to a metal element.

(3) The metal ion salt solution and the alkaline solution precipitant were added to a reactor at 60° C. to form a reaction system, and the reaction system was subjected to precipitation, to obtain a precipitated product, wherein a pH value of the reaction system was maintained at a range of 8 to 10.

(4) The precipitated product was aged at 70° C. for 24 h to obtain a ternary hydrotalcite-like.

(5) The ternary hydrotalcite-like was subjected to calcination (at 500° C. for 3 h) and activation (in 5 vol % $H_2$/Ar) in sequence.

The succinic acid used in Examples 1 to 7 was commercially available bio-based succinic acid.

Examples 1 to 7

Raw materials were weighed according to raw material dosages in Table 1 and a resulting mixture was then subjected to esterification, wherein an esterification temperature was shown in Table 1. A resulting oligomer polyester was introduced into a hydrogenation reactor and directly subjected to hydrogenation, wherein 1 ton of a catalyst was fed to react with 500 tons of the oligomer polyester, and parameters of the hydrogenation are shown in Table 1. A 1,4-BDO crude product was obtained, and then rectified and purified at a pressure of 8 mmHg to 20 mmHg and a temperature of 140° C. to 190° C. to obtain bio-based 1,4-BDO.

As shown in Table 1, the succinic acid from a bio-based source and the alcohol compound are used as raw materials, and the target product bio-based 1,4-BDO is prepared by esterification and hydrogenation reduction, and the bio-based 1,4-BDO has a purity of ≥99.5%, a raw material conversion rate of ≥99.5%, and a 1,4-BDO selectivity of ≥98.0%.

TABLE 1

Reaction conditions, product purity, and product batch yield of Examples 1 to 7

| | Item | | | | | | | |
|---|---|---|---|---|---|---|---|---|
| Item | Succinic acid dosage/g | Raw material 1,4-BDO dosage/g | Esterification temperature/° C. | Hydrogenation reduction pressure/MPa | Hydrogenation reduction temperature/° C. | Selectivity of hydrogenation reduction of 1,4-BDO | 1,4-BDO purity | 1,4-BDO yield/g |
| Example 1 | 5000 | 5500 | 205 | 8 | 220 | 98.11% | 99.52% | 7305 |
| Example 2 | 5000 | 5900 | 197 | 10 | 210 | 98.08% | 99.56% | 7731 |
| Example 3 | 5000 | 6300 | 190 | 12 | 200 | 98.20% | 99.53% | 8082 |
| Example 4 | 5000 | 6700 | 182 | 14 | 190 | 98.32% | 99.67% | 8465 |
| Example 5 | 5000 | 7100 | 175 | 16 | 180 | 98.41% | 99.63% | 8842 |
| Example 6 | 5000 | 7500 | 168 | 18 | 170 | 98.36% | 99.57% | 9193 |
| Example 7 | 5000 | 7900 | 160 | 20 | 160 | 98.05% | 99.54% | 9566 |

Examples 8 to 14

These examples were the same as Example 1, except that during the preparation of the catalyst, the calcination was conducted at 600° C.

TABLE 2

Reaction conditions, product purity, and product batch yield of Examples 8 to 14

| Item | Succinic acid dosage/g | Raw material 1,4-BDO dosage/g | Esterification temperature/° C. | Hydrogenation reduction pressure/MPa | Hydrogenation reduction temperature/° C. | Selectivity of hydrogenation reduction of 1,4-BDO | 1,4-BDO purity | 1,4-BDO yield/g |
|---|---|---|---|---|---|---|---|---|
| Example 8 | 5000 | 5500 | 205 | 8 | 220 | 97.90% | 99.22% | 7268 |
| Example 9 | 5000 | 5900 | 197 | 10 | 210 | 97.88% | 99.16% | 7669 |
| Example 10 | 5000 | 6300 | 190 | 12 | 200 | 97.98% | 99.23% | 8035 |
| Example 11 | 5000 | 6700 | 182 | 14 | 190 | 98.12% | 99.47% | 8426 |
| Example 12 | 5000 | 7100 | 175 | 16 | 180 | 98.21% | 99.43% | 8798 |
| Example 13 | 5000 | 7500 | 168 | 18 | 170 | 97.97% | 99.37% | 9133 |
| Example 14 | 5000 | 7900 | 160 | 20 | 160 | 97.85% | 99.24% | 9509 |

As shown in Table 2, the succinic acid from a bio-based source and alcohol compound are used as raw materials, and the target product bio-based 1,4-BDO is prepared by esterification and hydrogenation reduction, and the bio-based 1,4-BDO has a purity of ≥99.1%, a raw material conversion rate of ≥99.5%, and a 1,4-BDO selectivity of ≥97.8%.

Examples 15 to 21

These examples were the same as Example 1, except that 2.7 mol of copper nitrate hexahydrate, 1 mol of aluminum nitrate nonahydrate, and 0.7 mol of zinc nitrate hexahydrate were used during the preparation of the catalyst.

TABLE 3

Reaction conditions, and product purity and yield of Examples 15 to 21

| Item | Succinic acid dosage/g | Raw material 1,4- BDO dosage/g | Esterification temperature/° C. | Hydrogenation reduction pressure/MPa | Hydrogenation reduction temperature/° C. | Selectivity of hydrogenation reduction of 1,4-BDO | 1,4-BDO purity | 1,4-BDO yield/g |
|---|---|---|---|---|---|---|---|---|
| Example 15 | 5000 | 5500 | 205 | 8 | 220 | 97.89% | 99.20% | 7259 |
| Example 16 | 5000 | 5900 | 197 | 10 | 210 | 97.86% | 99.19% | 7660 |
| Example 17 | 5000 | 6300 | 190 | 12 | 200 | 97.93% | 99.25% | 8031 |
| Example 18 | 5000 | 6700 | 182 | 14 | 190 | 98.06% | 99.38% | 8428 |
| Example 19 | 5000 | 7100 | 175 | 16 | 180 | 98.15% | 99.35% | 8784 |
| Example 20 | 5000 | 7500 | 168 | 18 | 170 | 97.95% | 99.31% | 9139 |
| Example 21 | 5000 | 7900 | 160 | 20 | 160 | 97.82% | 99.26% | 9512 |

As shown in Table 3, the succinic acid from a bio-based source and alcohol compound are used as raw materials, and the target product bio-based 1,4-BDO is prepared by esterification and hydrogenation reduction, and the bio-based 1,4-BDO has a purity of ≥99.1%, a raw material conversion rate of ≥99.5%, and a 1,4-BDO selectivity of ≥97.8%.

Moreover, by comparing the data in Tables 1 to 3, it can be seen that the catalyst of the present disclosure has a high metal loading capacity. The surface morphology and the physicochemical properties of the supported copper-based catalyst could be modified by regulating the active metal ratio and the calcination temperature, so that the catalyst has a higher specific surface area, greater metal dispersion, suitable surface acidity and alkalinity, and desirable $Cu^{+}/Cu^{0}$ ratio. Therefore, the catalytic hydrogenation of the oligomer polyester could achieve a lower hydrogenation pressure, lower hydrogenation temperature, and lower hydrogen-to-ester ratio, thereby further improving the conversion rate of the oligomer polyester and the selectivity of the 1,4-BDO.

The above described are merely preferred embodiments of the present disclosure rather than limitations to the present disclosure in any form. It should be noted that those of ordinary skill in the art may further make several improvements and modifications without departing from the principle of the present disclosure, but such improvements and modifications should be deemed as falling within the scope of the present disclosure.

What is claimed is:

1. A method for preparing bio-based 1,4-butanediol (BDO), comprising:

mixing succinic acid from a bio-based source and an alcohol compound to obtain a mixture, and subjecting the mixture to esterification to obtain an oligomer polyester; wherein the succinic acid from the bio-based source is derived from biological fermentation;

subjecting the oligomer polyester to hydrogenation reduction in the presence of a catalyst to obtain a 1,4-BDO crude product; wherein a molar ratio of hydrogen used in the hydrogenation reduction to the oligomer polyester is in a range of 80-200:1; the catalyst is a supported copper-based catalyst, the supported copper-based catalyst is prepared by a process comprising the following steps:

(1) mixing copper nitrate hexahydrate, aluminum nitrate nonahydrate, an active metal salt, and water to obtain a metal ion salt solution, wherein a metal in the active metal salt is selected from the group consisting of manganese, nickel, cobalt, zinc, cerium, and zirconium, wherein a molar ratio of the copper nitrate hexahydrate, the metal in the active metal salt, and the aluminum nitrate nonahydrate is in a range of 2.7:0.7:1 to 5:1:2;

(2) mixing sodium hydroxide, sodium carbonate, and water to obtain an alkaline solution precipitant;

(3) adding the metal ion salt solution and the alkaline solution precipitant to a reactor at 60° C. to form a reaction system, and subjecting the reaction system to precipitation to obtain a precipitated product, wherein a pH value of the reaction system is maintained at a range of 8 to 10;

(4) aging the precipitated product at 70° C. for 24 h to obtain a ternary hydrotalcite-like compound; and (5) subjecting the ternary hydrotalcite-like compound to calcination and activation in sequence to obtain the supported copper-based catalyst, the calcination being conducted at a temperature of 500° C. to 600° C. for 0.5 h to 8 h; and purifying the 1,4-BDO crude product to obtain the bio-based 1,4-BDO.

2. The method of claim 1, wherein the alcohol compound is one or more selected from the group consisting of ethylene glycol and 1,4-BDO.

3. The method of claim 1, wherein a molar ratio of the succinic acid from the bio-based source to the alcohol compound is in a range of 1:1.2-2.4.

4. The method of claim 1, wherein the esterification is conducted at a temperature of 160° C. to 210° C. for 4 h to 8 h.

5. The method of claim 1 wherein the hydrogenation reduction is conducted at a pressure of 1 MPa to 20 MPa and a temperature of 100° C. to 220° C. for 2 h to 6 h.

6. The method of claim 2, wherein a molar ratio of the succinic acid from the bio-based source to the alcohol compound is in a range of 1:1.2-2.4.

7. The method of claim 2, wherein the esterification is conducted at a temperature of 160° C. to 210° C. for 4 h to 8 h.

* * * * *